United States Patent [19]

Krbechek

[11] 4,252,731
[45] Feb. 24, 1981

[54] PREPARATION OF STEROIDAL CARBAMATES

[75] Inventor: Leroy O. Krbechek, Minneapolis, Minn.

[73] Assignee: Henkel Corporation, Minneapolis, Minn.

[21] Appl. No.: 122,395

[22] Filed: Feb. 19, 1980

[51] Int. Cl.³ .............................................. C07J 1/00
[52] U.S. Cl. ............................... 260/397.3; 260/397.1
[58] Field of Search ........................... 260/397.3, 397.1

[56] References Cited

U.S. PATENT DOCUMENTS

| | | | |
|---|---|---|---|
| 3,149,102 | 9/1964 | Georgian et al. | 268/239.5 |
| 3,340,255 | 9/1967 | Javregg et al. | 260/239.55 |

OTHER PUBLICATIONS

Julian et al., "JACS" (1948) No. 3, pp. 887–892.

*Primary Examiner*—Elbert L. Roberts
*Attorney, Agent, or Firm*—Forrest L. Collins; Patrick J. Span

[57] ABSTRACT

The present invention describes a process for converting the amides of certain steroids to the corresponding carbamates of the steroid.

13 Claims, No Drawings

PREPARATION OF STEROIDAL CARBAMATES

BACKGROUND OF THE INVENTION

1. Field of the Invention

This invention describes technology useful for obtaining progesterone and progesterone-related compounds from steroids having a 20-carboxamido functionality.

2. Description of the Art

It is known that progesterone and progesterone-like compounds can be made through a variety of routes. In the present invention, 20-carboxamido compounds are utilized to form progesterone and its analogs. One route utilizing an acid functionality on the steroid side chain is reported in an article entitled, "The Conversion of Hyodesoxycholic Acid to Progesterone," by Bharucha, et al, as reported in the *Canadian Journal of Chemistry*, Vol. 34, 1956 at page 982–990. The Bharucha, et al, route also utilizes N-bromosuccinimide as one of the reactants in this process. Another route utilizing an acid, this time a 20-carboxy acid of a steroid to obtain progesterone via the Oppenauer oxidation is reported by Wieland, et al, in Helvetica Chimica Acta, Vol. XXXII, Part VI (1949), No. 255 at page 1922–1933. Wieland again with his coauthor Mischler in Helvetica Chimica Acta, Vol. XXXII, Part V (1949), No. 233 at pages 1764–1769 again reports a method for obtaining progesterone through a complicated route utilizing a 20-carboxy steroid compound.

Julian, et al, in an article entitled, "Delta 20-pregnenes from Bisnor-Steroid Acids," as reported in JACS at Vol. LXX, published 1948, No. 3, at pages 887–892, reports that 20-carboxy steroids may be converted to useful steroids. In another article published in Helvetica Chimica Acta at Vol. XXXII, Part V (1949), No. 232 at pages 1758–1763, Meystre, et al, report that 20-carboxy steroid compounds may be converted to the corresponding chloroamine and thereafter, through a multi-step reaction, progesterone may be obtained. U.S. Pat. No. 3,519,658 issued to Adam, et al, July 7, 1970 discusses the use of N-chlorosuccinimide with steroids.

Useful steroids having a 20-carboxyl functionality are described in European Patent application 4-913 published Oct. 31, 1979. An additional useful product obtained therein is 3-oxo-pregna-1,4,17(20)-triene-20-carboxylic acid. More useful acids are described in U.S. Pat. No. 3,994,933 issued to Jiu, et al, Nov. 30, 1976.

The present invention, however, overcomes a number of difficulties involved in the previous reactions in that the progesterone may be obtained directly without protection of the unsaturation in the A ring of the steroid structure and without the need to utilize chemical compounds to protect or interconvert the 3-keto functionality on the A ring.

Throughout the specification and claims, percentages and ratios are given by weight and temperatures are in degrees Celsius unless otherwise indicated.

SUMMARY OF THE INVENTION

The present invention describes a process of converting a member selected from the group consisting of 3-oxo-pregna-1,4-diene- 20-carboxylic acid amide; 3ox-o-pregn4-ene-20-carboxylic acid amide; 3-oxo-pregna-1,4,17(20)-triene-20-carboxylic acid amide; and 3-oxo-pregna-4,17(20)-diene-20-carboxylic acid amide; and mixtures thereof to the corresponding 20-methyl carbamate compound comprising the steps of:

(a) contacting the acid amide with a source of bromine thereby forming the corresponding bromoamide;

(b) reacting the compound formed in step (a) with a strong base thereby forming the corresponding 20-isocyanate; and (c) reacting the 20-isocyanate in the presence of methanol, to give the corresponding 20-methyl carbamate compound.

DETAILED DESCRIPTION OF THE INVENTION

The present invention utilizes as a starting material (A) 3-oxo-pregna-1,4-diene-20-carboxylic acid amide; (B) 3oxo-pregn-4-ene-20-carboxylic acid amide; (C) 3-oxo-pregna-1,4,17(20)-triene-20-carboxylic acid amide, and (D) 3-oxo-pregna-4,17(20)-diene-20-carboxylic acid amide and mixtures thereof to obtain the desired compound.

These carboxyamido compounds are obtained from the corresponding 20-carboxylic acids which may be obtained as suggested in the Jiu U.S. Pat. No. 3,994,993, issued Nov. 30, 1976 herein incorporated by reference. Some of the starting materials for the present invention may be obtained through the technology embodied in European Patent application 4-913 published Oct. 31, 1979, herein incorporated by reference. In any event, the starting acids are obtainable and may be converted to the carboxyamido compounds of the present invention through conversion to the corresponding carbonyl chloride of the acid and then reacted with ammonia to give the starting amide for the present invention.

Having obtained the particular 20-carboxyamido steroid compounds described above, this material is then reacted with any material which will provide a source of bromine which is necessary to form the bromoamide of the starting material.

Coveniently, the source of bromine will be elemental bromine, although any material which will produce bromine or a positive bromine ion to form the bromoamide is a suitable material herein. The conditions for forming the bromoamide compound include dissolving the carboxyamido compound in a methanol which functions as a reactant and a solvent. Conveniently, a cosolvent will be employed such as a halogenated hydrocarbon, i.e. methylene chloride or ethylene dichloride. The mixed solvent systems are conveniently employed in a weight ratio of one to the other of from 15:1 to 1:10 of the alcohol to the cosolvent, however, there must be sufficient alcohol as a reactant in any case. The use of a strong base such as sodium hydroxide, potassium hydroxide, or sodium methoxide, or mixtures thereof is necessary to generate the bromoamide. An additional material which may be included at this point in the reaction process is a urethane-forming catalyst, such as dibutyl tin dilaurate.

The reaction mixture containing at a minimum the carboxyamido compound and the solvent system is then conveniently treated to exclude oxygen such as by bubbling an inert gas through the reaction mixture to drive off all oxygen in the system. Dry nitrogen gas is conveniently used as the method of obtaining an inert atmosphere.

The reaction mixture then has the source of bromine, conveniently elemental bromine, added over a period of time in amounts sufficient to form the bromoamide. The amount of bromine utilized is simply that required to form an equivalent amount of the bromoamide. In practice, however, it is convenient to utilize at least 1.1 equivalents of the source of bromine, preferably at least 1.3 equivalents of the bromine to ensure completeness of the reaction.

The source of bromine is added generally over a period of about five minutes to avoid having the reaction become too vigorous. At this point it should be mentioned that it is surprising that the bromine does not add to the double bonds which are prevalent in the steroid ring system and, in some cases, at the 17(20) position of the steroid molecule. It should also be noted that an extremely strong base is required in this reaction as weaker bases do not provide sufficient strength to liberate one of the amine hydrogens from the carboxyamido compound, there by allowing the bromoamide to be formed. Thus the entire reaction presents a paradox. It must be sufficiently vigorous with the bromine to add to the molecule in the desired position, but not so vigorous as to generate unwanted substituents at the site of unsaturation in the steroid molecule.

Following addition of the bromine, the resultant mixture is stirred for a period of about one hour to ensure complete reaction. Thereafter, the reaction mixture is acidified with a week acid such as acetic acid and thereafter the solvent present is removed at reduced pressure. The material obtained therefrom is the crude 20-methyl carbamate. The reaction is essentially a one step process from the amide to the carbamate which is conveniently conducted at from about 0° C. to about 60° C.

Shown below at A–D are the generic structural formulas of the present invention.

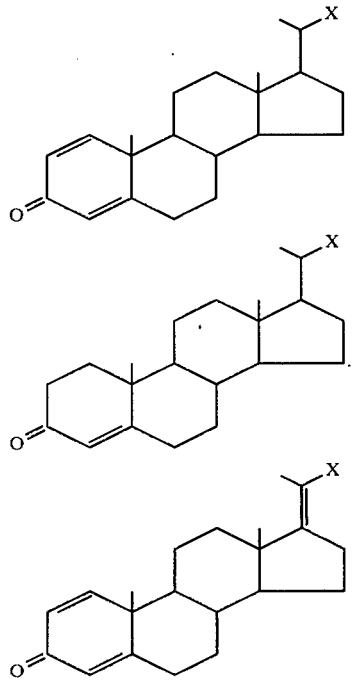

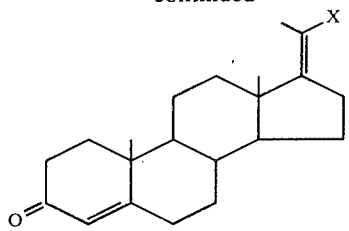

Where X is COOH, the starting acid is shown (the ester may be used but requires conversion to the acid). Where X is COCl, the acid halide (chloride) is indicated.

Where X is $CONH_2$ describes the amide and CONHBr the bromoamide is shown. The methyl carbamate is shown as X being $NH(CO_2)CH_3$ and the intermediate isocyanate formed in the reaction is NCO.

The methyl carbamate compounds may then be purified through washing with an organic solvent such as methylene chloride and then further treated successively with water, a scavenger such as a thiosulfate salt, followed by water washing. The product may then be dried with a suitable drying agent such as calcium sulfate and the solvent removed at reduced pressure.

The following are examples of the present invention.

EXAMPLE I

Three hundred and forty-three grams of 3-oxo-pregn-4-ene carboxylic acid amide is dissolved in 7.5 liters of methanol containing 162 grams of sodium methoxide and 750 milliliters of methylene chloride. Ten grams of dibutyl tin dilaurate are also added as a urethane forming catalyst. The reaction mixture is placed under a nitrogen atmosphere, stirred at room temperature for approximately 15 minutes at which time 240 grams of elemental bromine are added over approximately 5 minutes.

The resultant mixture obtained above is stirred for a period of approximately one hour followed by acidification with 250 milliliters of acetic acid. The solvents present are then removed at reduced pressure. The residue is dissolved in methylene chloride and washed successively with water, sodium thiosulfate and water. Following drying with calcium sulfate, the solvent is removed at reduced pressure to leave 390 grams of crude product which analyzed for greater than 70% of the corresponding methyl carbamate of the steroidal acid amide. A small portion of the residual amide was found in the reaction product.

The above example may be modified through using other strong bases such as sodium hydroxide or potassium hydroxide. It is noted, however, that sodium methoxide appears to work best in the present reaction. In similar fashion, the remaining acid amides are converted to the methyl esters of 3-oxo-pregna-1,4-diene-20-carbamic acid; 3-oxo-pregna-1,4,17(20)-triene- 20-carbamic acid; and 3-oxo-pregna-4,17(20)-diene-20-carbamic acid.

What is claimed is:

1. The process of converting a member selected from the group consisting of 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide; and mixtures thereof to the corresponding 20-methyl carbamate compound comprising the steps of:
 (a) contacting the acid amide with a source of bromine thereby forming the corresponding bromoamide;
 (b) reacting the compound formed in step (a) with a strong base thereby forming the corresponding 20-isocyanate; and
 (c) reacting the 20-isocyanate in the presence of methanol, to give the corresponding 20-methyl carbamate compound.

2. The process of claim 1 wherein the base is selected from the group consisting of sodium hydroxide, potassium hydroxide, and sodium methoxide and mixtures thereof.

3. The process of claim 1 additionally comprising a urethane forming catalyst to aid in the formation of the 20-carbamate compound.

4. The process of claim 3 wherein the urethane forming catalyst is dibutyl tin dilaurate.

5. The process of claim 1 which conducted in an inert atmosphere.

6. The process of claim 1 wherein a solvent system which consists essentially of methanol and methylene chloride is employed.

7. The process of claim 1 wherein the source of bromine is elemental bromine.

8. The process of claim 5 wherein the inert atmosphere is nitrogen.

9. The process of claim 1 wherein step (c) is followed by acidification.

10. The process of claim 9 wherein the acid employed is acetic acid.

11. The process of claim 1 wherein step (c) is followed by treatment with a reducing agent.

12. The process of claim 1 wherein the strong base is sodium methoxide.

13. The process of claim 1 which is conducted at from about 0° Celsius to about 60° Celsius.

* * * * *